United States Patent [19]

Kanda et al.

[11] Patent Number: 4,563,898
[45] Date of Patent: Jan. 14, 1986

[54] ACOUSTIC MICROSCOPE

[75] Inventors: Hiroshi Kanda, Tokorozawa; Kageyoshi Katakura, Meguro; Isao Ishikawa, Hino, all of Japan

[73] Assignee: Hitachi, Ltd., Tokyo, Japan

[21] Appl. No.: 586,806

[22] Filed: Mar. 6, 1984

[30] Foreign Application Priority Data

Mar. 7, 1983 [JP] Japan ................................. 58-35828

[51] Int. Cl.⁴ ............................................. G01N 29/00
[52] U.S. Cl. ....................................... 73/606; 73/599; 73/615; 73/629; 73/634
[58] Field of Search ................... 73/599, 606, 607, 615, 73/629, 634

[56] References Cited

U.S. PATENT DOCUMENTS

| 4,378,699 | 4/1983 | Wickramasinghe | 73/606 |
| 4,420,979 | 12/1983 | Momii et al. | 73/606 |
| 4,487,069 | 12/1984 | Ishikawa et al. | 73/606 |

FOREIGN PATENT DOCUMENTS

57-191543 11/1982 Japan ..................................... 73/606

Primary Examiner—Howard A. Birmiel
Attorney, Agent, or Firm—Antonelli, Terry & Wands

[57] ABSTRACT

An acoustic microscope comprising an acoustic transducer which performs both generation and detection of acoustic wave beams, and a sample holding member which opposes to an acoustic wave transmitting and receiving surface of the transducer, to hold an object sample through an acoustic wave propagating medium and to offer behind the sample a layer of an acoustic impedance unequal to that of the sample, so that the sample holding member is moved in parallel, thereby to detect acoustic waves reflected from front and rear surfaces of the sample and acoustic waves reflected from a surface of the sample holding member without reaching the sample and to measure amplitudes and returning periods of time of the reflected acoustic waves, so as to measure the velocity of sound through the sample of unknown thickness, the acoustic impedance of the sample, etc. from the measured values.

8 Claims, 16 Drawing Figures

ACOUSTIC MICROSCOPE

BACKGROUND OF THE INVENTION

1. Field of the Invention

The present invention relates to means to measure the elastic physical quantity of a sample in an imaging device which utilizes high-frequency acoustic energy, particularly an acoustic microscope.

2. Description of the Prior Art

A scanning acoustic microscope (abbreviated to "SAM") utilizing a very-high-frequency acoustic wave whose acoustic frequency is 1 GHz, accordingly whose acoustic wavelength in water is as short as approximately 1 micron, has been proposed in U.S. Pat. No. 4028933 by way of example.

The acoustic microscope produces an acoustic beam converging into a focal region of very small area by the use of an acoustic lens having a large numerical aperture F and mechanically scans a sample to-be-imaged which is held in and near the focal region, while it detects disturbed acoustic waves from the sample so as to obtain an image indicative of the distribution of elastic behaviors of the sample on the basis of the detection signal.

As one purpose of the acoustic microscope, it has been proposed to measure the elastic property of an observed sample. An acoustic beam having entered the sample is subject to such disturbances as reflection, refraction and transmission attenuation. The reflection of the beam is principally determined by the acoustic impedance of the sample, and the refraction and the attenuation are respectively determined by the velocity of sound through the sample and the attenuation constant of the sample. Accordingly, values indicative of the elastic properties of the sample can be obtained by measuring disturbed acoustic waves from the sample.

Such acoustic microscopes are generally of two types: the type which detects a reflected wave from a sample (the reflection type) and the type which detects an acoustic wave transmitted through a sample (the transmission type). The former can use a single transducer for both the generation and the detection of acoustic wave beams. In contrast, the latter requires individual transducers for the respective operations and needs to set these transducers at confocal positions, resulting in the disadvantage that the adjustment of the alignment of these transducers is difficult. Meanwhile, since the two phenomena of refraction and transmission attenuation of the acoustic wave beam by the sample pertain essentially to the transmission of the acoustic wave, measurements of the velocity of sound through the sample and the attenuation constant of the sample have been impossible with the prior-art acoustic microscope of the reflection type.

On the other hand, the transmission type acoustic microscope has been subject to the restriction that the velocity of sound and the attenuation constant through and of the sample can be measured only when the thickness of the sample is known.

SUMMARY OF THE INVENTION

An object of the present invention is to provide means to generate, in effect, the phenomena of refraction and attenuation having hitherto been attained with a transmission type setup, in spite of the use of a reflection type setup so as to measure the physical constants of the velocity of sound through and the attenuation constant of a sample.

Another object of the present invention is to provide an acoustic microscope which can measure the velocity of sound through and the attenuation constant of a sample even when the thickness of the sample is unknown.

The present invention consists of an acoustic microscope comprising an acoustic transducer which performs both the generation and detection of acoustic wave beams, and a sample holding member which opposes the acoustic wave transmitting and receiving surface of the transducer to hold a sample with an acoustic wave propagation medium intervening therebetween and to offer behind the sample a layer of an acoustic impedance unequal to that of the sample, so that the amplitudes and the returning periods of time of acoustic waves reflected from the front and rear surfaces of the sample and acoustic waves reflected from the surface of the sample holding member without passing through the sample are measured from the outputs of the transducer, thereby to obtain the elastic physical quantities of the sample.

DETAILED DESCRIPTION OF THE INVENTION

Figure 1:
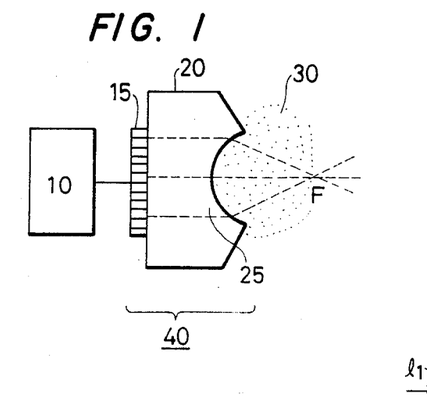
FIG. 1 is a sectional view of an acoustic transducer for use in an embodiment of the present invention.

The structure and function of a typical acoustic transducer 40 employed in an acoustic microscope will be described with reference to FIG. 1. One end of a cylindrical crystal 20 of sapphire or the like is polished into a flat surface on which a piezoelectric film 15 is formed. The other surface is formed with a semipherical concave surface. The members 20 and 15 constitute the acoustic transducer 40. An RF electric signal is applied from a signal source 10 to generate an RF acoustic plane wve within the crystal 20. The plane acoustic wave is converged on a predetermined focus F by a positive lens which utilizes the difference of sonic velocities through the crystal 20 and a medium 30 (usually, water) at the interface 25 of these constituents 20, 30 formed at the concave surface. As is well known, when the ratio between the focal distance and the aperture diameter, namely, the F number expressive of the brightness of a lens is sufficiently small, a remarkably narrow acoustic wave beam can be produced by this arrangement.

Figure 2:
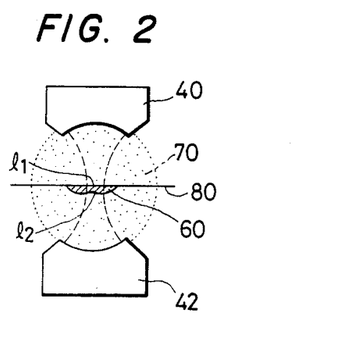
FIG. 2 is a sectional view of a conventional acoustic wave detecting structure.

FIG. 2 shows the setup of an acoustic wave detecting portion in a transmission type acoustic microscope for the sake of comparison with a setup in accordance with the present invention. Besides a transducer 40 as shown in FIG. 1, another transducer 42 similar thereto is opposed and arranged in confocal fashion, whereby an acoustic wave transmitted through a sample 60 is detected by the transducer 42. The biological sample 60 or the like is stuck on the rear side of a sample holder 80, which typically has been provided as a thin Mylar film fastened on a metal frame. The reason is that, since the acoustic impedance of the Mylar film is nearly equal to that of water, the presence of the supporting film has a negligible effect on the measurement result.

With such a transmission type setup, when the sample 60 is set and when not, the periods of time in which an acoustic wave having started from the transducer 40 arrives at the transducer 42 and the amplitudes of the detection signals are respectively measured. In addition, the thickness of the sample 60 is separately measured. Then, the velocity of sound v through the sample 60, the attenuation constant α of the sample, etc. can be determined.

Meanwhile, the present invention consists in providing a sample holder for supporting a sample in order to obtain a signal equivalent to a transmission signal obtained with the transmission type setup, but by means of a reflection type setup which uses the single transducer for the generation and detection of the acoustic wave beams.

Figure 3:
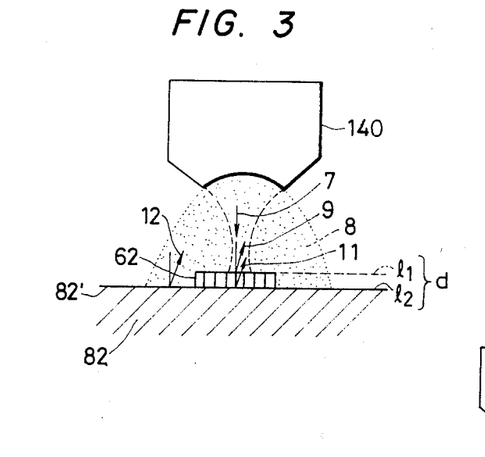
FIG. 3 is a sectional view of an acoustic wave detecting structure in the present invention.

FIG. 3 shows the setup of the acoustic wave detecting portion in the present invention. Both the generation and detection of acoustic waves are performed by a transducer 140. Behind a sample 62, there is formed a layer 82 of glass, metal, air or the like which serves as a total-reflection member as viewed from the water 8 and the sample 62. In the case where glass, metal or the like is employed for the layer 82 making up the total-reflection member, the layer 82 itself forms the holder for holding the sample. On the other hand, in the case where air is employed as the layer 82, a very thin film having an acoustic impedance substantially equal to that of water or the sample, for example, a Mylar film 82' is used as the sample holder.

An acoustic wave beam 7 entering from above the sample is partly reflected by the upper surface $l_1$ of the sample, and is mostly propagated into the sample 62. The acoustic wave propagated through the sample 62 is reflected by the interface $l_2$ between the layer 82 and the sample 62, is propagated through the sample again upwards, emerges in the water 8 through the interface $l_1$, and is detected as a reflected acoustic wave by the transducer 140. Here, the reflection at the interface $l_2$ is almost a total reflection, and the corresponding reflection signal 11 is very great. In addition, this reflection signal 11 is considered to have undergone the same disturbances as in transmitting the acoustic wave twice through the sample.

Figure 4:
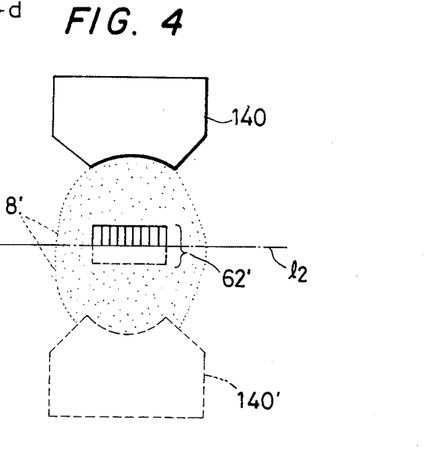
FIG. 4 is a sectional view showing the operation of the structure in FIG. 3.

Stated differently, the setup of FIG. 3 is equivalent to a setup as shown in FIG. 4 wherein a sample 62', which is twice as thick as the sample 62' lies within the water 8' between two transducers 140 and 140', positioned to oppose each other in confocal fashion with respect to a mirror plane $l_2$. It is accordingly understood that a signal similar to the signal obtained by the conventional transmission type setup can be detected by the setup of FIG. 3.

In order to acknowledge the above point and to compare the method of the invention with the conventional method, the conditions of propagation of acoustic waves in the transmission type setup and the present setup were theoretically studied. Here, since the sample lies on the focal plane of the transducer, the acoustic wave beam is considered to enter the sample perpendicularly. It is also considered that the interface of the biological sample is sufficiently diffused-like, and multiple reflection within the sample is negligible. With the conventional transmission type setup, the response of an impulse acoustic wave having entered such a sample is given by:

reflected wave:

$$v_{refl}(t) = K r \delta\left(t - \frac{2L - 2d_s}{v_w}\right) + K r (1 - r^2)e^{-2\alpha_s d_s} \cdot \delta\left(t - \frac{2L - 2d_s}{v_w} - \frac{2d_s}{v_s}\right) \quad (1)$$

transmitted wave:

$$v_{trans}(t) = K (1 - r^2)e^{-\alpha_s d_s} \delta\left(t - \frac{L' - d_s}{v_w} - \frac{d_s}{v_s}\right) \quad (2)$$

With the setup of FIG. 3, it is given by:

$$v'_{refl}(t) = K r \delta\left(t - \frac{2L - 2d_s}{v_w}\right) + K (1 - r^2)e^{-2\alpha_s d_s} \cdot \delta\left(t - \frac{2L - 2d_s}{v_w} - \frac{2d_s}{v_s}\right) \quad (3)$$

Here, Z, v, d and α denote the acoustic impedance, sonic velocity, thickness and attenuation constant, respectively. In addition, suffixes s and w denote the sample and water, respectively. L denotes the distance between the lens and the total-reflection plate of the present setup (the distance between the lens and the rear surface $l_2$ of the sample in the conventional setup), while L' denotes the distance between the opposing lenses. Besides, K is the device constant of the microscope system. r indicates the coefficient of reflection between the water and the sample and is given by:

$$r = (Z_s - Z_w)/(Z_s + Z_w) \quad (4)$$

The first terms of Equations (1) and (3) express the reflected waves from the front surfaces (boundaries $l_1$) of the samples (the reflected wave 9 in the case of FIG. 3), while the second terms of Equations (1) and (3) express the reflected waves from the rear surfaces (boundaries $l_2$) of the samples (the reflected wave 11 in the case of FIG. 3). Effects produced by lining the rear surface of the sample with the total-reflection member will become apparent by comparing the second terms of Equations (1) and (3). That is, the second term with the conventional setup is:

$$r (1 - r^2)e^{-2\alpha_s d_s} \delta\left(t - \frac{2L - 2d_s}{v_w} - \frac{2d_s}{v_s}\right)$$

whereas that with the setup of the present invention is:

$$(1 - r^2)e^{-2\alpha_s d_s} \delta\left(t - \frac{2L - 2d_s}{v_w} - \frac{2d_s}{v_s}\right)$$

First, the setup of the present invention does not undergo a decrease of the reflected wave due to the fact that the acoustic impedance of the organism forming the sample is close to that of water, accordingly r is small. Secondly, the signal $e^{-2\alpha_s d_s}$ pertaining to the attenuation $\alpha_s$ obtained by the transmission signal of the conventional setup can be consequently grasped as a sufficiently intense signal in spite of the reflection type setup.

It is accordingly understood that the reflection signal of the biological sample lined with the layer which can be be regarded as a total-reflection body is equivalent to the transmission signal of the biological sample lined with the soft material as in the prior art, and that the contrast attained by the invention is improved by a power of two (refer to Equation (2)).

Accordingly, when an image is picked up by the use of this reflection signal, the difficulty of the conventional setup is eliminated, that is, an image having blurs on account of the pile of the fine tissue structures of the organic sample is avoided. This signifies that a similar contrast is attained even with a thinner organic sample, which indicates the great effect of the present invention.

Further, when the setup of the present invention is used, the acoustic properties of the organic sample can be measured. First, the measurement of the velocity of sound through the sample will be explained. In the setup of FIG. 3, the time difference $\Delta t_1$ between the reflected wave 9 from the front surface ($l_1$) of the sample and the reflected wave 11 from the rear surface ($l_2$) is given from Equation (1) as follows:

$$\Delta t_1 = 2d_s/v_s \tag{5}$$

Accordingly, when the difference $\Delta t_1$ is measured by the transducer 140 and the thickness $d_s$ of the sample is measured by another means, the sonic velocity through the sample is obtained in accordance with Equation (5).

Further, with the setup of FIG. 3, the thickness of the sample can be simultaneously obtained. Accordingly, even in a case where the thickness $d_s$ is unknown, the sonic velocity through the sample can be measured. In this measurement, a reflected wave 12 from the reflection body 82 itself is used besides the respective reflected waves 9 and 11 from the front and rear surfaces of the sample. The reflected wave 12 from the reflection member 82 can be detected by oscillating the acoustic wave after the sample holding member (82 or 82′) has been mechanically moved in the lateral direction. The impulse response is given by:

$$v''_{refl}(t) = K \delta\left(t - \frac{2L}{v_w}\right) \tag{6}$$

$\Delta t_2$ which is the difference between the period of time from the oscillation of the acoustic wave to the detection of the reflected wave 12 and the period of time from the same to the detection of the foregoing wave 11 reflected from the rear surface of the sample, is given from Equations (3) and (6) as follows:

$$\Delta t_2 = \frac{2 d_s}{v_w} - \frac{2 d_s}{v_s} \tag{7}$$

Therefore, the thickness $d_s$ of the sample and the sonic velocity $v_s$ through the sample can be determined using the measured values of the two time differences $\Delta t_1$ and $\Delta t_2$ and the known sonic velocity $v_w$ through the water in accordance with the following relationships:

$$v_s = v_w \left(\frac{\Delta t_2 + \Delta t_1}{\Delta t_1}\right) \tag{8}$$

$$d_s = \left(\frac{\Delta t_2 + \Delta t_1}{2}\right) v_w \tag{9}$$

It is to be emphasized that, in this case, $d_s$ need not be evaluated independently by another means.

Moreover, according to the present invention, the amplitude of such reflected wave 12 from the reflector 82 can be used as a magnitude for calibrating the references of various reflected waves, and other physical constants, namely, the acoustic impedance and the attenuation constant can also be evaluated. Since the reflected wave 12 (Equation (6)) from the reflector 82 itself for lining the sample is independent of the property of the sample, the intensity of this signal is determined by only the device constant K. Letting $A_1$ denote the amplitude of the reflected wave 12, $A_2$ the amplitude of the reflected wave 9 from the front surface $l_1$ of the sample, and $A_3$ the amplitude of the reflected wave 11 from the rear surface $l_2$ of the sample, they are expressed from Equation (3) as follows:

$$A_1 = K \tag{10a}$$

$$A_2 = Kr \tag{10b}$$

$$A_3 = K(1 - r^2)e^{-2\alpha_s d_s} \tag{10c}$$

Accordingly, when the amplitudes $A_2$ and $A_3$ are normalized by the intensity $A_1$ of the reflected wave 12 from the total-reflection member, the following is obtained:

$$A_2/A_1 = r \tag{11a}$$

$$A_3/A_1 = (1 - r^2)e^{-2\alpha_s d_s} \tag{11b}$$

From Equation (11a), $$r = \frac{Z_s - Z_w}{Z_s + Z_w} = A_2/A_1$$

Therefore, the following is obtained:

$$Z_s = \left(\frac{1 + A_2/A_1}{1 - A_2/A_1}\right) Z_w \tag{12}$$

The acoustic impedance $Z_s$ of the sample can accordingly be determined using the known acoustic impedance of the water and the amplitudes of the reflected waves 9 and 11.

From Equation (11b), the attenuation constant $\alpha_s$ of the sample can be obtained using the values $d_s$ and r already found and the amplitude $A_3$ of the reflected wave 11.

In this manner, the employment of one of the reflected waves as the reference signal is a useful and very practical expedient because the reflected wave does not depend upon the system constant or the acoustic power and the change of frequency.

As stated above, according to the setup of the present invention, the beam returning period of time and the amplitude of the reflected wave from the total-reflector are respectively utilized as the reference values of the period of time and the intensity, whereby the thickness $d_s$, sonic velocity $v_s$, acoustic impedance $Z_s$ and attenuation constant $\alpha_s$ of the sample can be simultaneously obtained in spite of use of the reflection type setup and these values may be obtained independently with only use of the acoustic microscope.

Now, there will be described embodiments of the sample holder for forming the layer 82 making up the reflection member behind the sample. First, when the holder itself is used as the reflector, the material of the holder may be a material having an acoustic impedance which is sufficiently higher than that of the organism forming the sample and whose magnitude is known. For example, a crystal plate of sapphire or a silicon wafer is mentioned. According to the inventors' experiment, slide glass for use in an optical microscope is also meritorious in the point that it is readily available at a low price.

Figure 5:
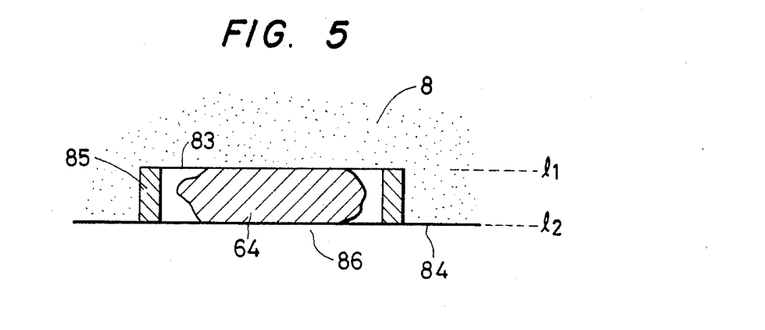
FIGS. 5 and 6 are sectional views each showing a sample holding portion in an embodiment of the present invention.

FIG. 5 shows another embodiment of the present invention. A sample 64 is sandwiched between two Mylar films 83 and 84, an air layer 86 is formed behind the more remote Mylar film 84 as viewed from the transducer, and the air layer 86 is used as a reflection member. The Mylar films 83, 84 are very thin, and the spacing thereof is determined by a spacer 85. The acoustic impedance of air is conspicuously low as compared with that of water 8 or the organic sample ($1.5 \times 10^6$ kg/cm²/s for the water, and $4 \times 10^2$ kg/cm²/s for the air), and the interface $l_2$ between them serves as the total-reflection body. Here, sandwiching the sample between the Mylar films produces two effects. First, the surface of the sample is flattened, whereby the degradation of the picture quality by the irregular reflection of the acoustic wave attributed to the unevenness of the surface can be prevented. Secondly, the contamination of the sample with another acoustically-meritorious material, such as mercury or alcohol, substituted for the water can be prevented.

Figure 6:
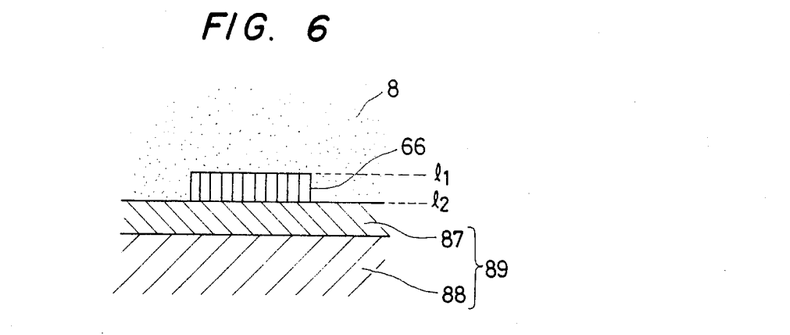

FIG. 6 shows still another embodiment of the present invention, in which a reflector of multilayer structure is used as the total-reflection member. In this embodiment of FIG. 6, a sample supporter 89 in which a layer 87 is disposed on a base 88 is used as the reflector. The layer constituting the supporter may well be replaced with two or more layers. A sample 66 is placed on the layer 87 so that, when the supporter 89 is viewed from the sample 66 or water 8, the acoustic impedance thereof may become sufficiently lower or sufficiently higher than that of the sample or the water. In actuality, letting the respective acoustic impedances of the layer 87 and base 88 be $Z_L$ and $Z_B$, the thickness of the layer 87 be d, and the wavelength of the acoustic wave used be $\lambda$, the acoustic impedance of the supporter 89 is given when the supporter is viewed from the sample side, by the following:

$$Z_{total} = Z_L \frac{Z_B \cos\theta + j Z_L \sin\theta}{Z_L \cos\theta + j Z_B \sin\theta} \quad (13)$$

where $$\theta = \frac{2\pi d}{\lambda} \quad (14)$$

Therefore, in case of using a material of high acoustic impedance, e.g., glass or metal for the base 88, when a high polymer or the like which exhibits a low acoustic impedance and which has a thickness of $d = \lambda/4$ is employed as the layer 87, Equations (13) and (14) become:

$$Z_{total} = \frac{Z_L^2}{Z_B} \quad (15)$$

and the acoustic impedance of the supporter becomes a very small value. In actuality, assuming $Z_L = 1.7 \times 10^6$ kg/cm²/sec (Mylar sheet) and $Z_B = 46 \times 10^6$ kg/cm²/sec (steel), the impedance $Z_{total}$ becomes $0.06 \times 10^6$ kg/cm²/sec, and as in the above embodiment, the supporter 89 can be deemed a total-reflector for the organic sample 66 or water 8 having $Z_S \simeq 1.5 \times 10^6$ kg/cm²/sec.

In addition, when the thickness of the layer 87 is set at $\lambda/2$, the impedance $Z_{total}$ becomes as follows from Equations (13) and (14):

$$Z_{total} = Z_B \quad (16)$$

Therefore, when metal or glass of high acoustic impedance is employed for the layer 87 and the thickness thereof is chosen to be $\lambda/2$, the base 88 may be formed of air.

That is, when the supporter made of the single layer of metal, glass or the like is used, it should desirably have the thickness of $\lambda/2$.

Next, an embodiment concerning means to discriminate the returning periods of time of the respective reflection signals in accordance with the present invention and means to measure the intensities of the reflection signals will be described with reference to FIG. 7.

When an RF pulse signal of a burst wave is applied from a gated RF oscillator 400 through a circulator 410 to a transducer which consists of a piezoelectric thin film 310 and an acoustic lens 320, so-called reflection echoes are obtained from a sample 350. FIG. 8 typically shows the time variation of the reflection waveform. In the figure, A indicates the RF pulses themselves, B the reflection echoes from the interface 330 between the lens 320 and water 340, and $C_1$ and $C_2$ the reflection echoes from the front surface and rear surface of the sample 350, respectively. These signals are converted into the video band by an RD detector 415, whereupon either reflection signal $C_1$ or $C_2$ is selected by an analog gate circuit 420. The converted signals are sampled by a sampling circuit 500, and the intensities of the desired reflected waves, in other words, $A_1$, $A_2$ and $A_3$ of Equations (10a), (10b) and (10c) can be known from a meter 505 which indicates the voltages of the signals. On the other hand, the output of the analog gate circuit 420 is amplified by an AGC amplifier 430, and the amplified voltage is copared with a reference voltage $V_R$ and shaped into a pulse by a comparator 440. This pulse is delayed by $\tau_M$ by a delay circuit 450, and the delayed pulse is used for causing the gated RF oscillator 400 to generate the burst RF pulse signal again. The repeating periods of the circulative operations based on such arrangement are detected by a counter 460. As indicated by a dotted line, the output pulse frequency of the delay circuit 450 may well be converted into a voltage by an F-V converter 470 so as to indicate the repeating period by indicating the voltage on a meter 475. Meanwhile, variable delay circuits 480 and 485 further delay the output pulse of the delay circuit 450 so as to form a gate pulse for the analog gate circuit 420 and a sampling pulse for the sampling circuit 500, respectively. A holder 82 which holds the sample 350 and which forms a reflection member can be moved in the lateral direction by scanning means 510. By driving the scanning means 510, reflection echoes from the holder 82 itself can also be detected.

Figure 9A:
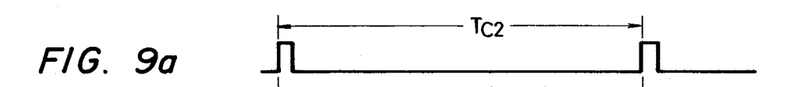
Figure 9B:
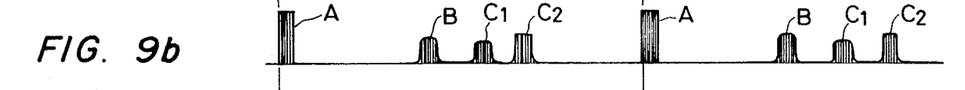
Figure 9C:
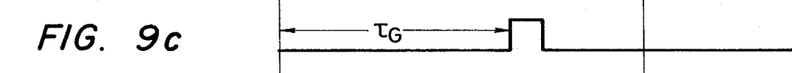
Figure 9D:
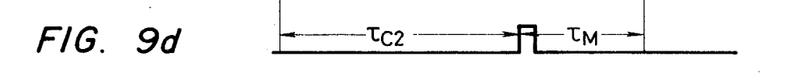
Figure 10A:
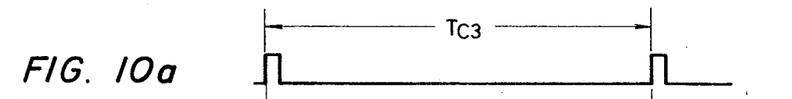
Figure 10B:
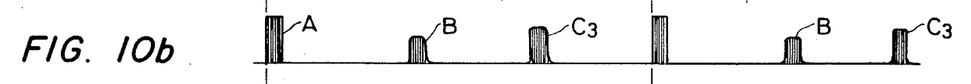
Figure 10C:
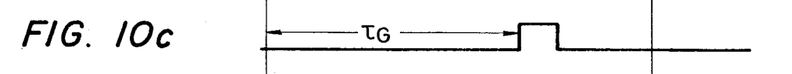
Figure 10D:
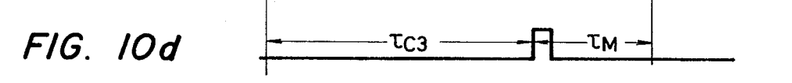

Now, circuit operations in the case of selecting the reflection signal $C_2$ from the rear surface of the sample by means of the analog gate circuit 420 will be explained with reference to FIGS. 9a-9d. When the delay time $\tau_G$ of the variable delay circuit 480 is adjusted as illustrated in FIG. 9c, the reflection echo $C_2$ among the reflection echoes shown in FIG. 9b is selected by the analog gate 420. Then, the output of the comparator 440 shown in FIG. 9d becomes a pulse which is delayed by the returning period of time $\tau_{C2}$ of the echo $C_2$ relative to the oscillated acoustic wave A of the RF generator 400. The output pulse is further delayed by the fixed time $\tau_M$ by the delay circuit 450, and becomes the gate pulse of the RF generator 400 again. Therefore, the period $T_{C2}$ of the output pulses of the delay circuit 450 as shown in FIG. 9a becomes the following:

$$T_{C2} = \tau_M + \tau_{C2} \tag{17}$$

Likewise, when the reflection echo $C_1$ is selected, the cycle $T_{C1}$ of the output pulses of the circuit 450 at that time is determined according to the returning period of tiem $\tau_{C1}$ of the reflection echo $C_1$, as follows:

$$T_{C1} = \tau_M + \tau_{C1} \tag{18}$$

Further, when the position of the holder 82 is horizontally moved and the reflection echo $C_3$ from the holder itself is detected and is selected by the analog gate, the repeating period $T_{C3}$ of the circuit 450 at that time is determined by the returning period of time $\tau_{C3}$ of the reflection echo $C_3$, as follows:

$$T_{C3} = \tau_M + \tau_{C3} \tag{19}$$

The waveforms of the respective parts in this case are shown in FIGS. 10a-10d.

Figure 7:
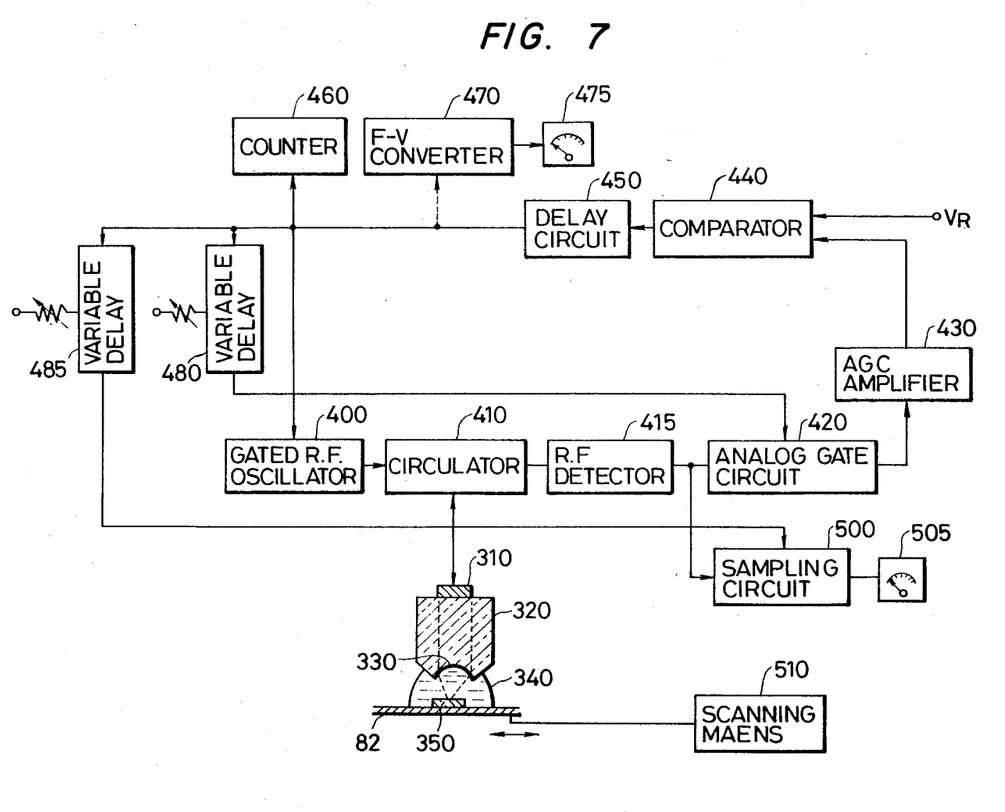
FIG. 7 is a block diagram showing the general arrangement of an embodiment of the present invention.
Figure 8:
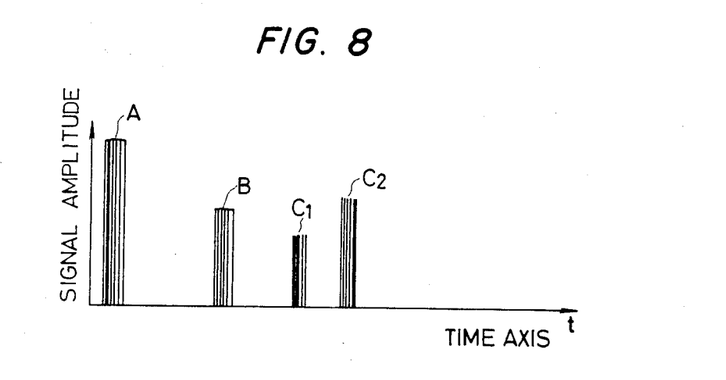
FIG. 8, FIGS. 9a–9d and FIGS. 10a–10d are time charts showing the operations of the embodiment in FIG. 7.

In this manner, the returning periods of time of the reflection echoes $C_1$, $C_2$ and $C_3$ can be respectively known from the measured values of the operating cycles of the circuit arrangement in FIG. 7 (the outputs of the counter 460 or the values indicated by the meter 475. The differences $\Delta t_1$ and $\Delta t_2$ of the returning periods of time in Equations (8) and (9) are respectively expressed by:

$$\Delta t_1 = T_{C2} - T_{C1} \tag{20}$$

$$\Delta t_2 = T_{C3} - T_{C2} \tag{21}$$

Therefore, the sonic velocity $v_s$ through and the thickness $d_s$ of the sample 350 can be directly obtained from these values of the operating cycles in accordance with the following equations:

$$v_s = v_w \left( \frac{T_{C3} - T_{C1}}{T_{C2} - T_{C1}} \right) \tag{22}$$

$$d_s = \left( \frac{T_{C3} - T_{C1}}{2} \right) v_w \tag{23}$$

It is to be added that cycle measuring means employing any well-known technique other than the examples illustrated in FIG. 7 may of course be used as long as it meets the objectives of the present invention.

We claim:

1. An acoustic microscope comprising:
   an acoustic transducer which performs both generation and detection of acoustic wave beams passing from and to said transducer by way of an acoustic wave transmitting and receiving surface thereof,
   a sample holding member which is positioned to oppose said acoustic wave transmitting and receiving surface of said transducer, so as to hold an object sample in an acoustic wave propagating medium disposed between said acoustic transducer and said sample holding member and providing behind the sample a layer of a material having an acoustic impedance unequal to that of the sample,
   mechanical means for moving said sample holding member laterally in a plane transverse to the axis of said transducer so that first acoustic waves reflected from a front surface and a rear surface of the sample and second acoustic waves reflected from a surface of said sample holding member without reaching the sample are detected by said transducer, and
   measuring means for measuring the amplitudes and the time periods of return of each of said first and second acoustic waves on the basis of the output signals of said transducer so as to determine the elastic physical quantities of said sample.

2. An acoustic microscope according to claim 1, wherein said sample holding member is made of a material which has an acoustic impedance higher than that of the sample.

3. An acoustic microscope, comprising:
   an acoustic transducer which performs both generation and detection of acoustic wave beams passing from and to said transducer by way of an acoustic wave transmitting and receiving surface thereof,
   a sample holding member which is positioned to oppose said acoustic wave transmitting and receiving surface of said transducer so as to hold an object sample in an acoustic wave propagating medium disposed between said acoustic transducer and said sample holding member and providing behind the sample a layer of a material having an acoustic impedance unequal to that of the sample,
   so that amplitudes and returning periods of time of acoustic waves reflected from a front surface and a rear surface of the sample and acoustic waves reflected from a surface of said sample holding member without reaching the same may be measured from outputs of said transducer so as to determine the elastic physical quantities of the sample, wherein said sample holding member is made of a material which has an acoustic impedance higher than that of the sample and has a thickness of $\lambda/2$, where $\lambda$ denotes a wavelength of the acoustic wave used.

4. An acoustic microscope according to claim 1, wherein said sample holding member is made of a thin film which has an acoustic impedance approximately equal to that of the sample and behind which an air layer is located.

5. An acoustic microscope according to claim 4, wherein said sample holding member further includes a film which covers the front surface of the sample.

6. An acoustic microscope according to claim 1, wherein said sample holding member has a multilayer structure.

7. An acoustic microscope comprising:
an acoustic transducer which performs both generation and detection of acoustic wave beams passing from and to said transducer by way of an acoustic wave transmitting and receiving surface thereof,
a sample holding member which is positioned to oppose said acoustic wave transmitting and receiving surface of said transducer, so as to hold an object sample in an acoustic wave propagating medium disposed between said acoustic transducer and said sample holding member and providing behind the sample a layer of a material having an acoustic impedance unequal to that of the sample,
so that amplitudes and returning periods of time of acoustic waves reflected from a front surface and a rear surface of the sample and acoustic waves reflected from a surface of said sample holding member without reaching the same may be measured from outputs of said transducer so as to determine the elastic physical quantities of the sample, wherein said sample holding member has a multilayer structure including a surface layer which has an acoustic impedance lower than that of an inner layer thereof and a thickness of $\lambda/4$, where $\lambda$ denotes a wavelength of the acoustic wave used.

8. An acoustic microscope comprising:
an acoustic transducer which performs both generation and detection of acoustic wave beams passing from and to said transducer by way of an acoustic wave transmitting and receiving surface thereof,
a sample holding member which is positioned to oppose said acoustic wave transmitting and receiving surface of said transducer, so as to hold an object sample in an acoustic wave propagating medium disposed between said acoustic transducer and said sample holding member and providing behind the sample a layer of a material having an acoustic impedance unequal to that of the sample,
mechanical means to move said sample holding member laterally in a plane transverse to the axis of said transducer so that first waves reflected from the front and rear surfaces of said sample and second waves reflected from a surface of said sample holding member without passing through the sample are detected by said transducer,
drive means for repeatedly driving said transducer in a pulsed fashion, the repeating period of driving thereof consisting of successively controlled periods respectively corresponding to the returning periods of time of each of said reflected waves detected by said transducer, and
measurement and indication means for measuring the repeating period of said drive means and the amplitudes of the signals detected by said transducer and for indicating the measured magnitudes thereof, so that the amplitudes and returning periods of time of said first and second reflected waves are successively obtained from the indicated values.

* * * * *